United States Patent [19]

Gawrisch et al.

[11] Patent Number: 4,692,026
[45] Date of Patent: Sep. 8, 1987

[54] PROCESS AND APPARATUS FOR CONTINUOUS DETERMINATION OF THE STATES OF ANISOTROPY OF OPTICALLY ACTIVE MATERIALS

[75] Inventors: Wolfgang Gawrisch, Gau-Bischofsheim; Walter Valentin, Hohenstein; Helmut Czepl, Eppstein, all of Fed. Rep. of Germany

[73] Assignee: Hoechst Aktiengesellschaft, Frankfurt am Main, Fed. Rep. of Germany

[21] Appl. No.: 777,979

[22] Filed: Sep. 19, 1985

[30] Foreign Application Priority Data

Sep. 25, 1984 [DE] Fed. Rep. of Germany ....... 3435059

[51] Int. Cl.$^4$ ................................. G01B 9/02
[52] U.S. Cl. ..................... 356/345; 356/351
[58] Field of Search ............ 356/345, 346, 349, 351, 356/357, 361, 365

[56] References Cited

U.S. PATENT DOCUMENTS 3,902,805  9/1975  Redner ............................. 356/365 X
4,443,106  4/1984  Yasuda et al. .................... 356/357
4,560,277  12/1985  Monzer ............................ 356/357

FOREIGN PATENT DOCUMENTS 0155142  9/1985  European Pat. Off. ............ 356/345
2338305  2/1975  Fed. Rep. of Germany .
2449475  4/1976  Fed. Rep. of Germany .
3106818  7/1982  Fed. Rep. of Germany .
3128306  2/1983  Fed. Rep. of Germany .

Primary Examiner—Eugene R. LaRoche
Assistant Examiner—Steven J. Mottola
Attorney, Agent, or Firm—James C. Lydon

[57] ABSTRACT

The orientation state of a film material is determined from the double refraction during the manufacturing process. A light source irradiates the film material to measure the path difference corresponding to the anisotropy of the film material. Interference patterns, created by one or more compensating wedges, are recorded by a photosensitive diode matrix. The individual electrical signals generated by the diode matrix are subjected to level discrimination by a discriminator and generated as binary images, each of which has a single interference stripe, which is evaluated. Interference patterns from different irradiation directions are simultaneously imaged next to each other and/or above one another. If an interference stripe cannot be found in a diode line, the system switches to the diode lines of the diode matrix which are above or below it. The thickness of the film material is measured and the double refraction calculated from it along with the path difference. The correlation of double refraction with different material properties such as strength, thermal conductivity, and compressibility provides information about material properties even during manufacture. All the data obtained are storable on data storage media and are used to control the system.

10 Claims, 13 Drawing Figures

PROCESS AND APPARATUS FOR CONTINUOUS DETERMINATION OF THE STATES OF ANISOTROPY OF OPTICALLY ACTIVE MATERIALS

BACKGROUND OF THE INVENTION

The present invention relates to a process and an apparatus for continuous determination of the states of anisotropy of optically active materials by means of their double refractions in one or more principal directions, wherein the path difference of interfering wave trains is generated with the aid of an optical compensator, with the thickness of the optically active material being measured simultaneously and an interference pattern generated by the compensator being evaluated photoelectrically as a function of position.

German Offenlegungsschrift No. 24 49 475 teaches such a process for determining the state of anisotropy of transparent or translucent polymers by measuring the orientation double refraction employing a compensator, which provides the path difference required for determining the double refraction. Photoelectronic analysis of the interference color pattern is employed to measure the path difference, said pattern being obtained behind an analyzer connected to the compensator, which is a wedge compensator. The path difference, which appears as an optically visible signal, is converted into an electrical signal with the aid of photosensitive components, photocells for example. At least two beam paths are evaluated to determine the degree of anisotropy, one of said paths preferably penetrating the sample under test vertically and the other, diagonally. The electrical signal corresponding to the optical path difference can be used to control the manufacturing process or for semi-continuous quality control with computer control. The device for measuring the orientation double refraction comprises a position-sensitive stripe detector which measures the total light intensity striking it with simultaneous indication of the location of maximum brightness. The stripe detector records the interference pattern obtained by the compensator. Instead of a stripe detector, a multiple detector can also be used in which the individual detectors are interrogated by means of a control logic individually as a function of the light intensities received from the interference color pattern and the detector, which receives the maximum intensity, shows the path difference or the phase shift through the optically active material through which the light passes. Similarly, one or more photosensitive elements can be provided to measure the optical path difference, said elements receiving the interference color pattern and being moved electromechanically by means of the compensator to determine the location of maximum brightness with parallel polarizers or maximum darkness with crossed polarizers.

The compensating wedge used in this process as a compensator is known. The compensating wedge covers a certain range of the path difference and generates a black stripe when traversed by light with crossed polarizers and a white stripe when the polarizers are parallel, said stripe being referred to hereinbelow as the interference stripe of zero-th order. This stripe is flanked to left and right by interference color stripes of the zero-th to nth order. The position of the individual interference stripes can be read off, for example using a scale division in nanometers, mounted on the commercially available compensating wedge. When the compensating wedge and the optically active material, which simultaneously exhibits double refraction properties, are fitted together, the path differences of the compensating wedge and the material are added together so that the interference stripes of zero-th order is displaced on the compensating wedge. This local displacement is a direct measure of the path difference in the material. As far as continuous measurement of anisotropic properties is concerned, this poses the difficulty that inhomogeneities generally appear in optically active material such as biaxially stretched films, which can also indicate the start of tearing of the film material. These inhomogeneities then frequently produce a path difference which is so great that, as a result of the addition of this path difference to the path difference of the compensating wedge, the interference stripe of zero-th order migrates out of the measurement range of the compensating wedge. In practice the interference pattern on the compensating wedge may not contain any interference stripes of zero-th order. In such a situation the detector means—the stripe dector, the multiple detector, or a photosensitive element moved electromechanically over the compensating wedge—merely detect an interference color stripe (if there is in fact an interference color stripe) which is significantly less bright than the interference stripe zero-th order. Such an interference color stripe provides no information about the double refraction of the material. It is therefore obvious that, with the known method, the danger of tearing of a film web which is indicated by pronounced changes in the double refraction or the path difference, cannot be measured continuously and can only be detected within very narrow limits in order to counteract it in proper time. If the range of the compensating wedge is increased to measure the path difference in order to overcome this disadvantage, there will be considerable deterioration of the resolution of the individual interference stripes so that the photosensitive detectors are frequently incapable of pinpointing the location of maximum brightness or maximum darkness within the interference color pattern on the compensating wedge and therefore the path difference or double refraction cannot be calculated.

German Patent No. 23 38 305 teaches a method for determining linear double refraction in an optically active material, wherein the material is irradiated by linearly polarized light and the emergent light is detected in a polarization plane perpendicular to the polarization plane of the incident light, whereby at least one wavelength is measured in which the detected light is extinguished. The measuring device used for this purpose comprises a light source whose beam passes through a polarizer in which the required linearly polarized wave is generated, which then passes through the film to be measured and enters an analyzer, thence emerging into a detector system. The detector system can be designed as a prism or grating or an optical multichannel analyzer with a plurality of detectors. The light source emits monochromatic or white light. A compensating wedge for measuring the path difference created by the film is not provided. Finally, German Offenlegungsschrift 31 06 818 teaches a method for continuous determination of multiaxial orientation states of stretched films or plates by means of their principal double refraction values, wherein three laser beam paths are employed, generated by three lasers or by splitting one laser beam, one of which passes perpendicularly through the film and the others pass through it at inclinations such that the inclination planes are perpendicular to the film surface and contain the two main orientation directions. The phase differences of the laser beam intensities are continuously measured after passing through the film, a quarter-wave plate, and a rotating analyzer. The three main double refraction values of the film are measured continuously from the three phase differences, considering the two slope angles of the sloping laser beams and the film thickness, measured in another fashion. The measuring device comprises three lasers directed parallel through a suitable system of lenses or mirrors after passing through the film. The light beam from one laser strikes the film plane perpendicularly, while the beams from the other two lasers strike the film at an angle $\phi$ to the normal of the film. The light beam of one laser runs in a plane which contains the film normal and the principal stretching of the film, while the light beam from the other laser lies in a plane which is determined by the film normal and the transverse stretching direction of the film. The optical anisotropy of the stretched film elliptically polarizes the light beams emerging from the lasers which are initially linearly polarized. A quarter-wave plate beneath the film converts the elliptical polarizing of the three laser beams into a linear polarization. A rotating polarizing filter beneath the quarter-wave plate cancels out the beams when their polarization directions are perpendicular to the polarization direction of the polarization filter. The intensities of the laser beams are converted into periodic electrical signals by photosensitive detectors, said signals being phase-shifted with respect to one another. These phase shifts can be determined with the aid of two phase meters, with the third phase shift supplementing the other two to 0°. The double refraction values can be determined from the measured phase shifts in a computer and used directly as parameters for biaxial film orientation for controlling a film stretcher.

This known measuring device is costly to build because it uses three lasers or an optical system to split a single laser beam into three beams.

An object of the invention is to provide a measuring method and a measuring apparatus with which it is possible continuously to determine the double refraction values of an optically active material such as a mono- or biaxially stretched film and to detect the danger of imminent tearing of the film in proper time.

SUMMARY OF THE INVENTION

In one aspect, the present invention relates to a process for the continuous determination of the state of anisotropy of an optically active material comprising:
(i) irradiating a portion of a travelling optically active material with at least two beams of light such that path differences of interfering wave trains are generated by at least one optical compensator;
(ii) continuously imaging the interfering wave trains of the optically active material after the wave trains have passed through the compensator upon a photosensitive two dimensional diode matrix and converting said interference patterns into a plurality of electrical signals corresponding to the intensity of light impinging on each point in said photosensitive matrix;
(iii) separately comparing each of said plurality of electrical signals against an adjustable reference level for each point in said photosensitive matrices, such that said adjustable reference limit corresponds to the interference stripe of zero-th order in said respective interference pattern;
(iv) horizontally scanning the interference pattern according to a bright dark and dark-bright transition to the adjacent diode column;
(v) simultaneously measuring the thickness of said optically active material.

In another aspect, the present invention relates to an apparatus for the continuous determination of the state of anisotropy of an optically active material comprising:
(i) a light source;
(ii) a polarizer;
(iii) a compensating wedge;
(iv) an analyzer;
(v) means for photosensitive scanning of said analyzer wherein the optically visible transmission from said analyzer is scanned as a function of its point-wise brightness; and
(vi) a computer
in combination such that light from said light source passes sequentially through said polarizer, said compensating wedge, and said analyzer before striking said means for photosensitive scanning of said analyzer, wherein said light is converted into electrical signals which are sent to said computer.

DETAILED DESCRIPTION OF THE INVENTION

Figure 1:
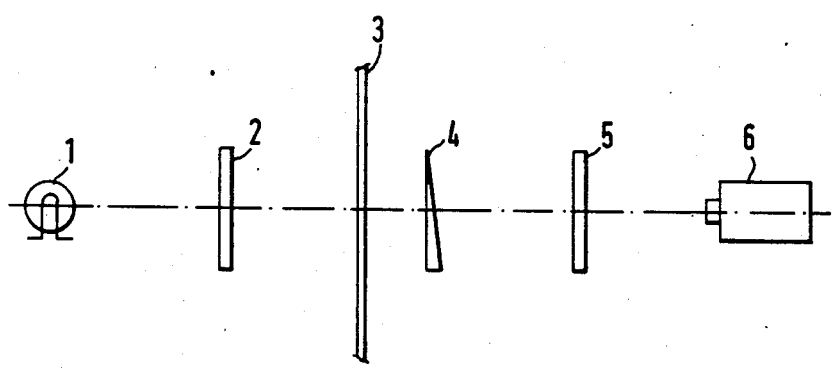
FIG. 1 is a schematic view of the measuring device of the invention.

The creation of double refraction is known and will be explained here only briefly.

An optically active material breaks up linearly polarized light into two mutually perpendicular directions, in which the two lightwave components have different propagation rates. For this reason, the two beams emerge from the double refracting material with a time lag between them and therefore have a phase difference of a certain magnitude. Upon emerging from the optically active material, the two lightwave components are added to one another to form a wave which, depending on the magnitude of the phase shift, can be polarized differently. If the path difference corresponds to a whole-number multiple of the wavelength of the lightwave, the emergent wave will simultaneously be linearly polarized and oscillate in the same plane as the linearly polarized incoming wave. If the light is polychromatic, no light will pass through an analyzer placed behind the double refracting material, if the polarization plane of said analyzer has been rotated through 90° to that of the polarizer. In such a situation the light is extinguished and a black interference stripe appears. Conversely, if the polarizer and analyzer are parallel to one another, the light will not be extinguished but instead, amplified, and an interference stripe with considerable brightness will appear.

If white, i.e. polychromatic light, is used, the complementary color of the extinguished color will appear. The path difference and the phase shift are linearly related and are a linear function of the path traveled by the lightwaves in the double refracting material. If the path difference $\Gamma$ is linked to the thickness D of the measured material, the double refraction $\Delta n$ will be $$\Delta n = \Gamma/D$$

The double refraction $\Delta n$ is the difference between the light refraction indices in the direction of anisotropy and perpendicular thereto.

The object of the invention is achieved by the method summarized above in which the interference pattern of the optically active material is imaged in each principal direction of a photosensitive two-dimensional matrix. The optical signals are converted into electrical signals by the matrix which are then subjected to a level discrimination in such a way that the electrical signal for each location on the matrix which corresponds to the interference stripe of zero-th order in the interference pattern is evaluated.

In an improvement on the invention, a plurality of interference patterns generated by compensating wedges with different optical path difference ranges, from each of the principal directions of the optically active material to be investigated, are imaged on the photosensitive two-dimensional matrix. The interference pattern of that compensating wedge which shows the greatest resolution for the individual interference stripes in its path difference range is then evaluated. The path difference ranges of the compensating wedges, depending on the absolute value, are of equal magnitude and the optical path difference ranges of the compensating wedges adjoin one another with an overlap of up to 12.5% of the individual path difference range.

In another embodiment of the invention, the interference patterns generated by the compensating wedges are imaged side by side and/or one above the other on a screen and switched to the individual interference patterns during scanning until an interference pattern with a single interference stripe of zero-th order is found.

The apparatus of the present invention comprises, in combination, a solid-state camera with a photosensitive x-y diode matrix capable of scanning the interference patterns generated by compensating wedges which are located in the beam path of a light source above the optically active material and an analyzer. The solid-state camera is connected to a computer. A monitor may be connected to the computer. The monitor's screen displays interference patterns corresponding to their point brightness as a function of the x-y position of the interference stripes of zero-th order.

In another embodiment of the invention, a discriminator is provided in the computer, said discriminator allowing only the electrical analog signals for point brightness of the light striking the diode in question that are above a certain level to pass through and discriminating all the analog signals below that value. In this manner the analog image of the interference pattern is converted into a binary image for the predetermined level, while all the analog signals and therefore the gray values which do not exceed a certain brightness are suppressed. The term "binary image" will always be understood in the following to refer to a brightness image without gray values, which contains a maximum of two brightness levels, for example, white and black. Moreover, a conventional thickness-measuring device is disposed in the immediate vicinity of the optical measuring device, said thickness-measuring device being connected to the computer to which it feeds the measured thickness of the material.

By means of the method and apparatus according to the invention, multiaxial orientation states of optically active transparent materials can be determined simultaneously and continuously by measuring the double refractions from the corresponding path difference which is determined with the aid of the compensating wedges, as can the local thickness of the optically active material. By means of a computer-supported, self-stabilizing evaluation of the interference stripe patterns, generated by compensation to a path difference of 0, in the optically active material in white light we can obtain information about current process-engineering parameters and anticipated physical properties in the material under test, to the extent that the correlations between these properties and the double refraction values are known. The method and the apparatus are simultaneously implemented advantageously at several points in the production process so that the relationship between the measured double refraction values and the process parameters and other material characteristics can be unambiguously pinpointed, so that continuous quality control in the moving material or the material web and process control are possible.

The operation of the compensating wedge method may be explained with reference to FIG. 1. Referring to FIG. 1, the light from a monochromatic or white light source 1 passes sequentially through a polarizer 2, the double refracting medium 3 to be investigated (for example, a monoaxially or biaxially stretched film made of a plastomer), a compensating wedge 4, and an analyzer 5, which advantageously has its polarization plane rotated by 90° to polarizer 2. The light then strikes an electronic camera 6, for example a solid-state camera, which has an x-y matrix composed of photosensitive diodes as a receiving surface. This diode matrix is evaluated by a special electronic circuit, not shown in such fashion that the optically visible interference pattern on compensating wedge 4 is scanned as a function of its point-wise brightness as a function of the position or x-y position of the individual diodes and can be viewed on a monitor.

The compensating wedge used in the compensation method is itself a double refracting medium, whose directions of anisotropy are crossed. The incident linearly polarized lightwave is refracted twice, i.e. broken down into one wave in the anisotropy direction and a wave perpendicular thereto. A total path difference 0 is obtained at the point of emergence of the wedge, at which the two velocity differences of the two waves are equal, so that a black stripe is obtained when the polarizers are crossed and a white stripe when they are parallel. Interference color stripes of the zero-th to nth order appear on the other wedge surface, but they are not black or white. When the double refracting compensating wedge interacts with a double refracting anisotropic material, the path differences of the compensating wedge and the material are added together. This results in a black or white line, hereinafter referred to as the zero-th-order interference stripe, being displaced on the compensating wedge. The local displacement of the black or white zero-th-order interference stripe is a direct measure of the path difference in the anisotropic material.

Figure 2A:
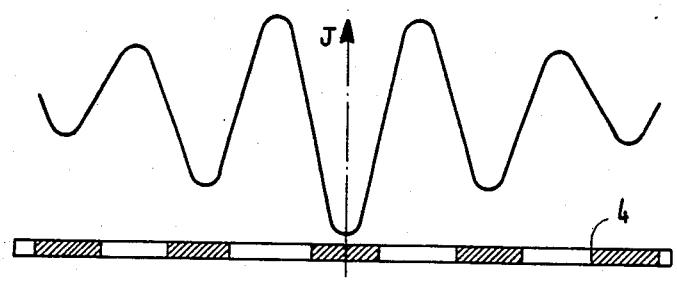
FIG. 2a is the intensity curve of an interference pattern which is formed by irradiating the optically active material on the compensating wedge of the measuring device according to FIG. 1.

FIG. 2a shows the intensity pattern of an interference curve on compensating wedge 4 in FIG. 1, which is indicated schematically below the interference curve with the interference stripes. When the polarizers are parallel to each other in the measuring device according to FIG. 1, the location of maximum brightness on compensating wedge 4 is a measure of the path difference. When the polarizers are crossed, it means that this is the location of maximum darkness, as shown in FIG. 2a. The interference stripe of maximum darkness, hereinafter referred to as zero-th-order interference stripe, is located symmetrically with respect to ordinate axis J and interference color stripes of zero-th to nth order are located symmetrically to the right and left of this stripe, with an intensity that decreases the further they are from the ordinate axis. The optical local signal of the interference pattern on the compensating wedge is converted into an electrical analog signal by the photosensitive diodes of the x-y diode matrix in solid-state camera 6. The electrical analog signal is then in turn converted into a binary image by means of an electronic circuit connected to the computer through a discriminator connected between them. The binary image is also displayed on a monitor connected to the computer. The discriminator changes the level, as decribed in greater detail with reference to FIGS. 2b to 2d.

Above a brightness level set by the discriminator, only the "bright" state is displayed. If a certain brightness is not exceeded by the interference curve after the level is adjusted, an intensity 0 is obtained, equivalent to the "dark" state; otherwise intensity 1 equivalent to the "bright" state is obtained, so that all gray values disappear.

Solely because of the difference between the two states in the subsequent processing of the electrical analog signal by the discriminator level change, the image thus produced is termed a "binary image."

Figure 2B:
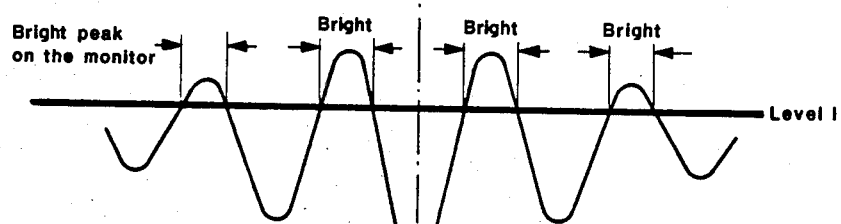
FIGS. 2b to 2d are the intensity curves of the interference pattern derived from the interference pattern shown in FIG. 2a by differential level discrimination of the electrical analog signals.
Figure 2C:
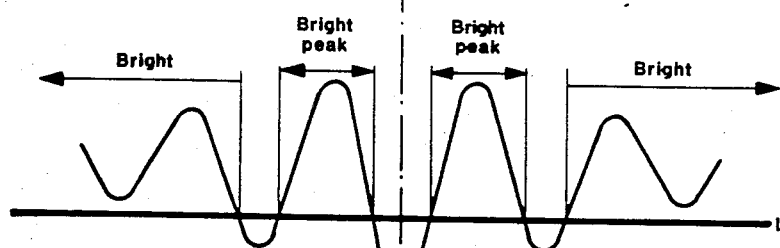
Figure 2D:
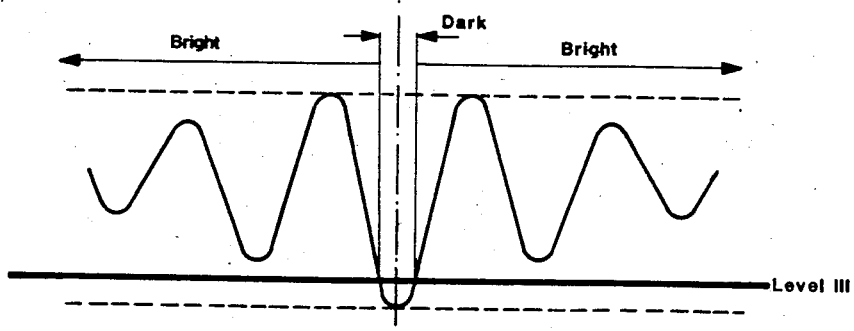

FIGS. 2b to 2d show the effects of threshold values of the discriminator of different levels with a transition from the black-and-white image to the binary image. The black-and-white image includes the gray values as well as the bright/dark level. At a level I there are closely delimited bright areas on the screen of the monitor, as shown in FIG. 2b. If, for example, the background of the screen of the monitor is kept bright, these bright areas will not be visible, but only the dark areas between them. If the threshold value is lowered to level II, the four bright areas will become wider, and the two outer bright areas will not be limited on the outside (FIG. 2c). If the threshold value is lowered even more to level III, a single dark area will remain in the middle of the interference curve, namely the zero-th-order interference stripe, while open bright areas will extend outward to the right and left of it. According to the invention, the zero-th order interference stripe is the only one used for evaluation because it can be clearly distinguished against the bright background of the monitor screen. Of course, the threshold value change on the discriminator can be carried out in the reverse order, i.e. the threshold value can be raised stepwise when the interference curve is recorded with the polarizers parallel to each other. In such a situation the location of maximum brightness on the compensating wedge is a measure of the path difference, and the screen background on the monitor is dark by comparison with the signal display.

Figure 3A:
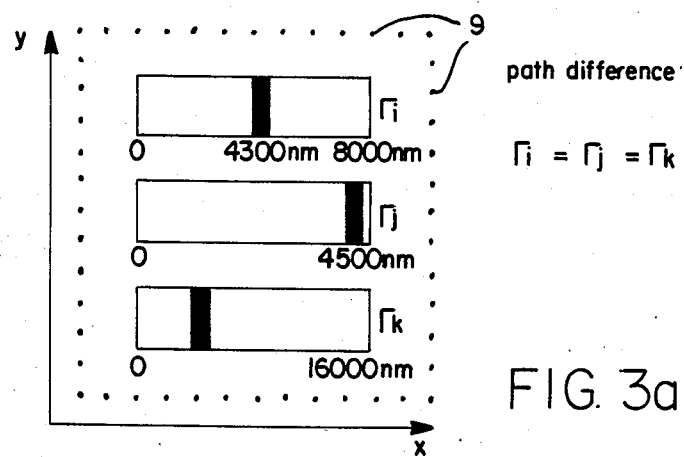
FIGS. 3a to 3c illustrate the images of the interference patterns of a plurality of compensating wedges on a photosensitive x-y diode matrix in a solid-state camera in the measuring device shown in FIG. 1.
Figure 3B:
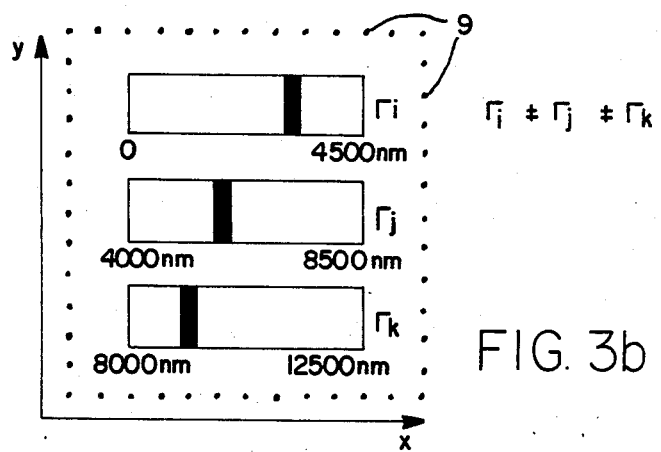
Figure 3C:
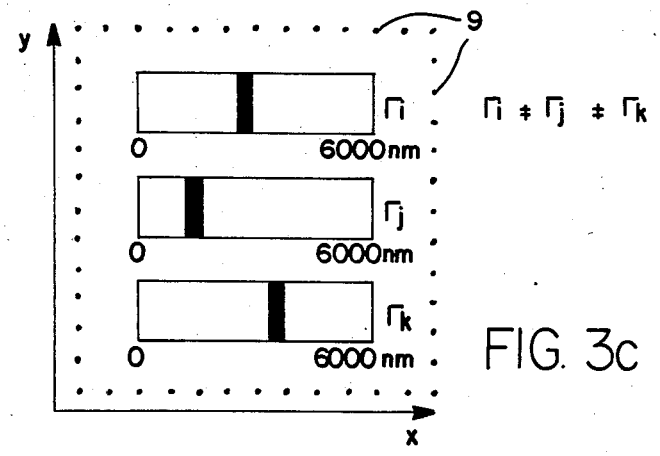

In FIGS. 3a to 3c, the x-y diode matrix 9 of the solid-state camera is shown schematically as well as the geometry of compensating wedges imaged one above the other on the diode matrix, with zero-th-order interference stripes in the specific x-stripe area of diode matrix 9. The position of the single zero-th-order interference stripe on the compensating wedge corresponds to a specific path difference λ, associated with a corresponding wavelength λ, in nanometers, for example, since, path difference $\Gamma = \lambda\Phi/2\pi$ with phase shift $\Phi$. Diode matrix 9 receives interference stripe of the zero-th order in a certain x-stripe range. According to the invention, compensating wedges may be used in the measuring device, located close together, said wedges being imaged next to and/or above one another on diode matrix 9. FIG. 3a, for example, shows three compensating wedges one above the other, which cover path difference ranges of different sizes, said ranges adjoining one another with a certain overlap. When the anisotropy of the optically active material is measured at the same point with each of these compensating wedges, the same path difference $\Gamma i = \Gamma j = \Gamma k$ will be obtained for the zero-th-order interference stripe. The position of the zero-th-order interference stripe in the interference pattern has a fixed relationship to the path difference, the phase shift, or the geometry of the compensating wedge, so that the above-mentioned path differences $\Gamma i$, $\Gamma j$, or $\Gamma k$ result from the x-position on diode matrix 9 of the solid-state camera. In FIG. 3a, for example, the upper wedge with its path difference $\Gamma i = 4300$ nm of the zero-th-order interference stripe covers a path difference range from 0 to 8000 nm, the middle compensating wedge with path difference $\Gamma j = \Gamma i$ covers a path difference range from 0 to 4500 nm, and the lower compensating wedge with path difference $\Gamma k = \Gamma j = \Gamma i$ covers a path difference range from 0 to 16,000 nm. It is obvious that the middle compensating wedge has the greatest resolution for path difference $\Gamma j$ of the zero-th-order interference stripe, since, of the three compensating wedges, from the standpoint of absolute value, it covers the smallest path difference range. Obviously, a compensating wedge which, for example, covers a path difference range from 6000 to 10,000 nm cannot detect this zero-th-order interference stripe.

In practice, the compensating wedges are selected so that their path difference or wavelength ranges adjoin one another with a slight overlap. For example, a first compensating wedge covers the wavelength range from 0 to 4500 nm, a second covers the wavelength range from 4000 to 8500 nm, and a third covers a wavelength range from 8000 to 12,500 nm. If in this wedge selection process, with the path difference ranges of the wedges being equivalent to the absolute value, the overlap range of 500 nm between two adjacent wedges is related to the non-overlapping absolute range of 4000 nm of the individual wedge, we get an overlap of 12.5%. This overlap is selected for safety reasons in order to ensure that even zero-th-order interference stripes with a path difference which is close to the compensating wedge which is adjacent to the boundary areas will be resolved satisfactorily.

FIGS. 3b shows three interference patterns, imaged on diode matrix 9, from compensating wedges with different path differences Γi≠Γj≠Γk. They are zero-th-order interference stripes, with each double refracting material being measured case at a different point. The compensating wedges therefore again cover path difference or wavelength ranges which adjoin one another with a slight overlap.

FIG. 3c is a diagram similar to that in FIG. 3b showing three interference patterns imaged on diode matrix 9 with different path differences Γi≠Γj≠Γk of the interference stripes of zero-th order. These are interference patterns that were measured with different double refracting materials at one and the same or at different spots.

In practice, for each measurement point, several compensating wedges or interference stripe patterns, and for each solid-state camera several measurement points, are imaged simultaneously next to each other and/or one above the other. Since several compensating wedges located physically close together are used, depending on the size of the path difference, the compensating wedge with the maximum resolution can be determined by means of a suitable computer program. This maximum resolution compensating wedge is then used to control the process. In the case shown in FIG. 3a, as previously stated, it would be the middle compensating wedge with path difference Γj that would produce the greatest resolution for subsequent processing.

Figure 4A:
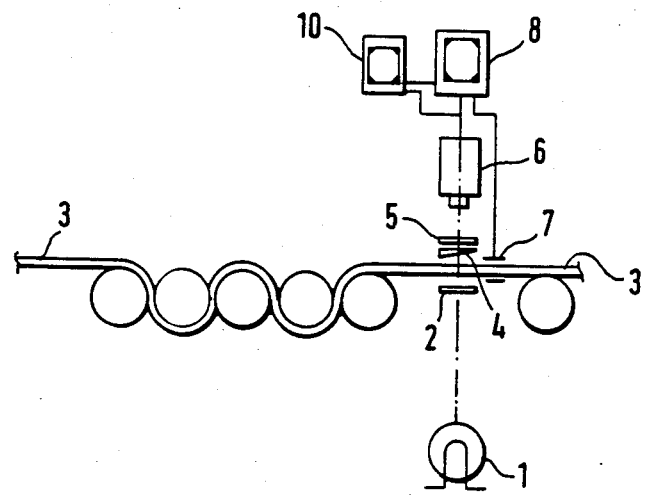
FIGS. 4a to 4c are schematic diagrams showing the measuring devices for the path difference produced by the optically active material and the thickness measurement of the optically active material during the manufacturing process.

FIG. 4a is a schematic representation of the design of a measuring device with a compensating wedge 4 and a thickness measuring device 7. The material under investigation, shown here as a moving, stretched polymer film 3 in a segment of a production process, passes through the measuring section represented by polarizers 2 and 5 and wedge 4, irradiated by light source 1. Solid-state camera 6 with an x-y diode matrix as a receiving surface, as shown in FIG. 3, is connected alternately directly and via computer 8 to monitor 10. The suitable thickness measuring device 7, known of itself, is located immediately adjacent to the optical measuring device, said device 7 likewise being connected to computer 8. Thickness measuring device 7 can be an infrared, isotope, measuring sensor, or a similar system.

The computer uses the path difference Γ on the basis of the interference pattern and the thickness D of the material under investigation to determine the double refraction:

$$\Delta n = \Gamma / D$$

Figure 4B:
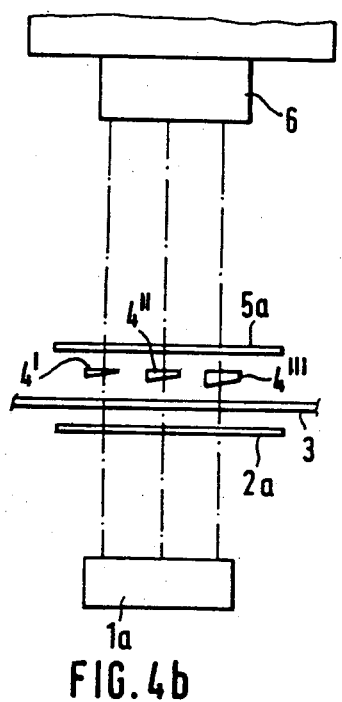

FIG. 4b is a schematic representation of an arrangement composed of three compensating wedges 4', 4", 4''' above film 3. Below the film is a common polarizer 2a for the three compensating wedges. A common flat radiator 1a irradiates polarizer 2a, the compensating wedges, and a common analyzer 5a and forms the interference patterns of the compensating wedges on the x-y diode matrix of camera 6 (see FIGS. 3a to 3c). The compensating wedges have geometrically equal lengths but different path difference ranges.

Figure 4C:
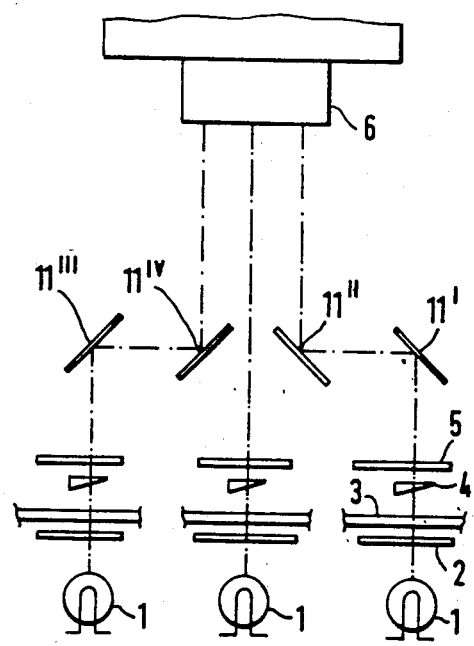

FIG. 4c is a schematic representation of the superimposition or imaging of measurement points spatially separate with the aid of mirror systems 11', 11", and 11''', 11$^{IV}$ on the x-y diode matrix of a common camera 6. Each measurement point is structured in the same way as shown in FIG. 4a. The single mirror system with two mutually parallel mirrors (which are pivotable) images the interference pattern of the compensating wedge on camera 6. At each individual measurement point, in turn, a plurality of compensating wedges can be provided, although not shown, in an arrangement like that shown in FIG. 4b.

Figure 5:
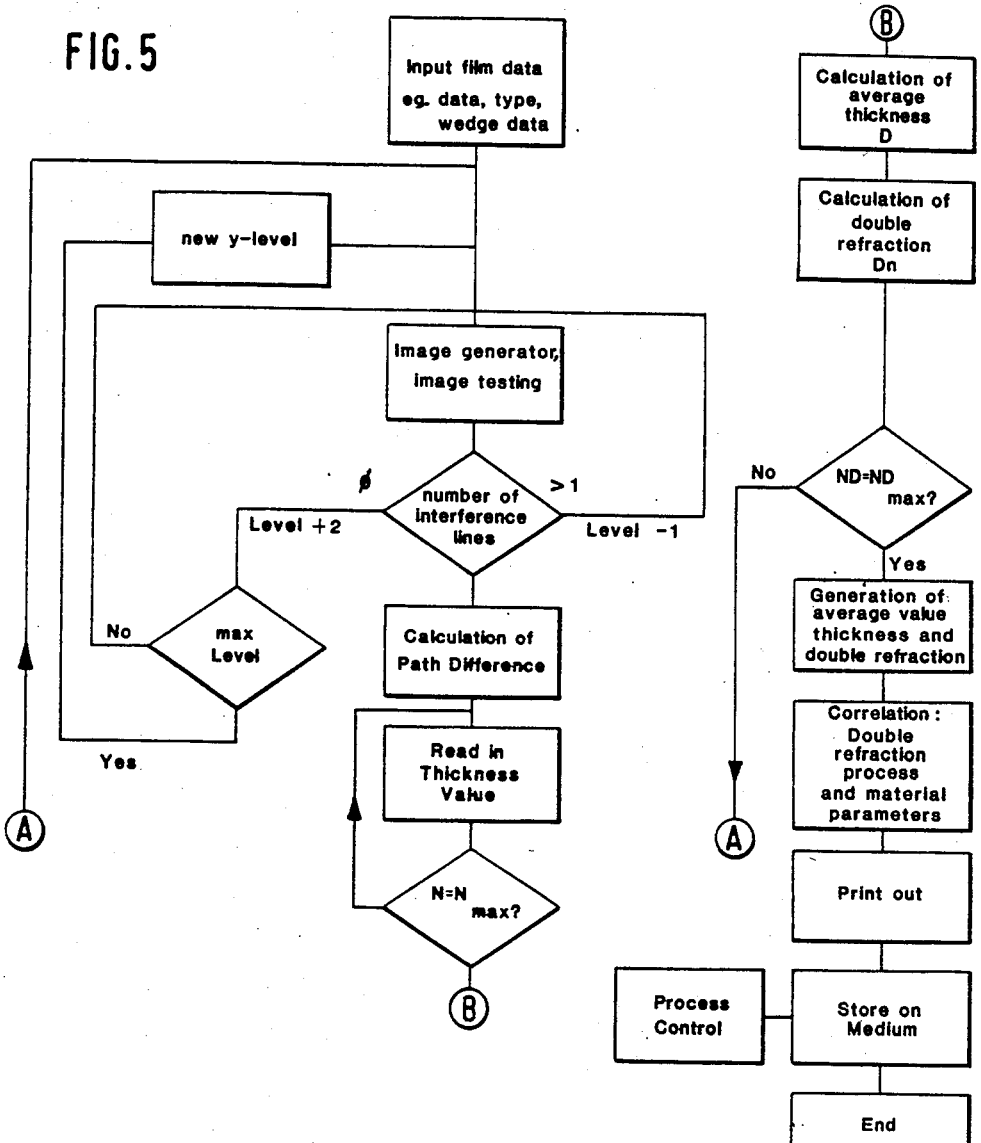
FIG. 5 is a flowchart describing the process that occurs in the computer of the measuring device according to FIG. 4 for image analysis.

FIG. 5 is a flowchart for controlling the computer 8. Certain data such as type of film, date of manufacture, and especially the positions of compensating wedges 4 relative to the receiving surface of the diode matrix, including data on the minimum and maximum compensating paths of the various compensating wedges, are initially entered. The image is then generated and checked for each individual interference pattern via the discriminator as a corresponding black-and-white image, which, in the final states, generates the binary image with only one interference stripe when the brightness level is correct. If the number of interference stripes is greater than one, so that an interference stripe pattern similar to that shown in FIGS. 2b and 2c is obtained on monitor 10 in FIG. 4, the level is lowered by one step and the program returns to the beginning of image generation and image checking. If no interference stripes at all are to be received by the solidstate camera from the first compensating wedge, the level is raised in two steps from the bottom. This level is compared with a maximum level to prevent the level from being raised too high, since over-radiation would then result in which the individual interference stripes of the interference pattern could not be detected (see FIG. 2a). If the raised level is below the maximum level, the image generation and image checking of the black-and-white image generated by the raised level begins again. If, on the other hand, the raised level is equal to the maximum level or exceeds it, the computer switches to the interference pattern generated with another compensating wedge 4 below it. In other words, a new y position is selected on the diode matrix of the solid-state camera. Then a new image generation and image checking process begins.

The image generation and image checking are performed in the manner described when several interference stripes or a single interference stripe is detected by the solid-state camera. The brightness level is varied over a predetermined path difference range until a single interference stripe is obtained in the binary image. Since the compensating wedges are selected so that one of the interference patterns will always produce the zero-th-order interference stripe, there is always an evaluation possibility with the process according to the invention. As soon as this individual zero-th-order interference stripe appears, the computer triggers calculation of the difference in path difference and the thickness values of the double refracting material are read in. In general, a continuous number of N thickness values is read in until a permanently programmed number $N_{max}$ of for example 50 thickness values is reached. As soon as this occurs, the thickness is calculated, namely the arithmetic mean of the $N_{max}$ thickness values is determined and calculation of double refraction is carried out using this arithmetic mean of the thicknesses. A number ND of double refractions is calculated until a permanently programmed number $ND_{max}$ of double refractions is obtained. So long as the permanently programmed number $ND_{max}$ is not reached, the system always goes back to the beginning of the program and goes through the individual program steps for a newly created image and the subsequent image test. As soon as the number ND of double refractions has reached the permanently programmed number $ND_{max}$, the average number of the double refraction is calculated and the correlation between the calculated double refraction and the permanently specified process and material parameters in the computer is determined. The correlation is printed out by the computer and stored on a data storage medium for checking, evaluation, and analysis. In addition, these measurement data thus obtained are used for process control and manufacture of the double refracting material, especially in film manufacture.

The measurement is carried out similarly when, instead of a single compensating wedge, several compensating wedges are used for different principal directions of the anisotropic double refracting material or several measuring devices are used at different points within the production facility.

The method can also be used for determining double refraction as a function of angle of incidence, as in extrapolation of the angle of incidence to 90° to determine the principal double refraction in the plane of the film. A mirror system $11'$, $11''$, or $11'''$, $11^{IV}$ (see FIG. 4c), which is varied at the same time the radiation direction is pivoted, then images the compensating wedge or wedges always in the same position on the diode matrix. Instead of the relatively costly guides for mirror system $11'$, $11''$, a separate pivoting camera system can be also be incorporated.

Calculation of principal double refraction in the film plane can also be handled easily by the available computer.

In practice, in evaluating measurement data obtained through determination of double refraction by known methods, as described German OS Nos. 24 49 475 and 31 06 818, considerable difficulties can arise, since in this case the procedure is always based on the theoretical intensity pattern within the interference pattern. Practice has shown however that, as a result of irregularities which can have a wide variety of different causes, such as sharp fluctuations in the film material caused by different orientation states, for example as a result of unfavorable temperature conditions during the production process, the intensity pattern in no way corresponds to the theoretical pattern at any point in the film, so that the interference stripes to be analyzed locally are subjected to strong and very irregular intensity variations. Known methods offer no way of compensating for such fluctuations so that, especially when they are used in critical production stages, they provide no results usable for process control. It is precisely the critical process stages, however, that require thorough analysis and control in order to counteract undesirable properties in the material.

Figure 6:
FIG. 6 is a schematic diagram showing an interference stripe of the zero-th order, interrupted by inhomogeneities, on a monitor in the measuring device according to FIG. 4.

FIG. 6 is a schematic diagram of the pattern of an interference stripe of zero-th order for a compensating wedge, as imaged on the diode matrix in practice. It always happens that, contrary to the theoretical continous pattern of interference stripes over several diode lines, there are interruptions in one or more diode lines caused by over-radiation or sharp variations in the properties of the material. If, in the binary digital image, no brightness transition from light to dark is found in the area of diode line $Y_n$ in the diode matrix, the system switches to lines $Y_n+i$ or $Y_n-i$, if changes in the discrimination level do not produce any imaging by the diode line $Y_n$. This is not possible using the essentially line-fixed systems for imaging and evaluation according to the state of the art. The lack of a zero-th-order interference stripe in the vicinity of diode line $Y_n$ would therefore produce no output signal or a false output signal.

The method in the device according to the invention, on the other hand, offers the guarantee that, even with rapid and locally severe fluctuations in intensity, measurements of the path difference of double refracting materials are possible. This is accomplished in two steps, namely:

a. By shifting the brightness level for the black-and-white image upward and downward until only one interference stripe is visible in the interference pattern, which extends over at least two gaps in the photosensitive diode matrix of the solid-state camera, for example over two gaps of $512 \times 256$ diode matrix. Two lines are the minimum since the image is interrogated after a transition from bright to dark and dark to bright in the adjacent columns in horizontal scanning.

b. If this minimum width of the imaged interference stripes is undershot, i.e. if the individual stripes become too narrow or disappear entirely, the system can switch to another y-diode line in the same image of the interference pattern on the diode matrix and a new scanning process can be triggered to determine the path difference. This is true even with a negative result for many diode lines in the photosensitive diode matrix as a result of unfavorable optical conditions as well as inhomogeneities in the material under test. The method therefore always offers the opportunity of determining the intensity patterns with maximum resolution. In short, the present invention optimizes and therefore detects by measuring techniques the path difference caused by the double refracting material.

EXAMPLES

The following examples are intended to illustrate the practice and advantages of the present invention. As such, these examples are illustrative only and are not intended to limit the scope of the claimed invention in any way.

The following are two numerical examples of measurements of double refraction of the film material and the relationship between double refraction and the thickness and strength or thickness alone.

EXAMPLE 1

During a stretching process in film production, the temperature in the stretcher was varied in five stages. In the immediate vicinity of the point where the path difference was measured, the thickness of the film was also determined and read into the computer through an A/D converter. The contrast variations which occurred in the binary interference patterns generated by the solid-state camera and the computer, caused by the rapid variations in the process parameter temperature, were easily recorded and used for analysis. Since the correlation between the double refraction and the strength values was permanently set in the computer, the anticipated strength could be calculated on the basis of the measured double refraction under these special production conditions. The average values given for thickness and double refraction refer to each of five individual measurements. The subsequent measurements of the strength values show very good agreement with the strength values calculated in advance and listed in the table.

TABLE I

| Measurement Number | Thickness (microns) | Temp. (°C.) | Double Refraction × $10^3$ | Strength (N/mm$^2$) |
|---|---|---|---|---|
| 1 | 11.1 | 128.0 | 11.5 | 102 |
| 2 | 10.8 | 122.0 | 17.1 | 123 |
| 3 | 10.9 | 117.0 | 29.1 | 162 |
| 4 | 11.7 | 114.6 | 33.6 | 178 |
| 5 | 12.1 | 112.0 | 39.0 | 196 |

EXAMPLE 2

During a production process for a refractive film, the lengthwise stretching ratio λ=3.4 was increased to λ=3.6. The lengthwise stretching ratio λ expresses the length ratio of the stretched film to the unstretched film. In order to obtain a constant thickness with a finished product, the feedstock supply rate was simultaneously increased by a factor of 3.6/3.4=1.05.

TABLE II

| Measurement Number | Time (min) | Thickness (microns) | Double Refraction × $10^3$ |
|---|---|---|---|
| 1 | 0 | 60.7 | 106 |
| 2 | 1 | 60.7 | 107 |
| 3 | 2 | 60.5 | 107 |
| 4 | 3 | 61.1 | 106 |
| 5 | 4 | 60.7 | 112 |
| 6 | 5 | 60.2 | 116 |
| 7 | 6 | 60.2 | 115 |
| 8 | 7 | 60.3 | 116 |
| 9 | 8 | 60.2 | 116 |
| 10 | 9 | 60.3 | 115 |

The transition phase from 3.4 to 3.6 started after measurement No. 4 and ended after measurement No. 6.

The evaluation of the irregularities that occur during the transition phase in the structure of the interference stripes could be carried out using the evaluation method without any problem.

We claim:

1. An apparatus for the continuous determination of the state of anisotropy of an optionally active material comprising:
   (i) a light source;
   (ii) a polarizer;
   (iii) a compensating wedge;
   (iv) an analyzer;
   (v) means for photosensitive scanning of said analyzer wherein the optically visible transmission from said analyzer is scanned as a function of its point-wise brightness; and
   (vi) a computer having a discriminator circuit; in combination such that light from said light source passes sequentially through said polarizer, said compensating wedge, and said analyzer before striking said means for photosensitive scanning of said analyzer, wherein said light is converted into electrical signals which are subsequently screened by said discriminator circuit so that higher than zeroth order interference stripes are not transmitted by said discriminator circuit and only the zeroth order interference stripe is operated on by said computer.

2. The apparatus of claim 1 including conventional means for determining the thickness of a travelling web, with the electrical output from said thickness determining means being sent to said computer via an analog/digital converter.

3. The apparatus of claim 1 wherein said discriminator is set so that every interference pattern sent from said compensating wedge is converted into a binary image having a single zero-th order interference stripe.

4. A process for automatic selection and continuous evaluation of the stripe of zero-th order of an interference pattern produced by a birefirngent polymeric film comprising:
   (i) irradiating a portion of a travelling birefringent polymeric film with linearly polarized light, thereby producing two lightwave components having a path difference T,
   (ii) summing the two lightwave components together to form an interference pattern by means of at least one compensanting wedge, so that T=0, thereby producing a plurality of interference stripes,
   (iii) passing the interference pattern through a second polarizer which is parallel to the polarization plane of said linearly polarized light,
   (iv) converting the optical intensity of the polarized interference pattern into a corresponding pattern of electrical intensity by means of a photosensitvie two-dimenisional diode matrix,
   (v) comparing said pattern of electrical intensity against an adjustable reference level so that only those interference stripes which have an electrical intensity greater than or equal to said reference level are not suppressed,
   (vi) determining the number of interference stripes which are not suppressed,
   (vii) continuously adjusting the adjustable reference level so that only the most intense interference stripe is not suppressed,
   (viii) continuously monitoring the translational movement, if any, of the most intense interference stripe.

5. The process of claim 4 wherein said pattern of electrical intensity is compared against siad adjustable reference level on a horizontal line-by-line basis.

6. The process of claim 5 wherein said adjustable reference level cannot exceed a pre-set maximum.

7. The process of claim 4 wherein at least two compensating wedges, each having a different optical path difference range, are employed.

8. A process for automatic selection and continuous evaluation of the stripe of zero-th order of an interference pattern produced by a birefrigent polymeric film comprising:
   (i) irradiating a portion of a travelling birefringent polymeric film with linearly polarized light, thereby producing two lightwave components having a path difference T,
   (ii) summing the two lightwave components together to form an interference pattern by means of at least one compensating wedge, so that T=0, thereby producing a plurality of interference stripes,
   (iii) passing the interference pattern through a second polarizer whose plane of polarization is 90° to the polarization plane of said linearly polarized light,
   (iv) converting the optical intensity of the polarized interference pattern into a corresponding pattern of electrical intensity by means of a pohotosensitive two-dimensional diode matrix, (v) comparing said pattern of electrical intensity against an adjustable reference level so that only those portions of said pattern which have an electrical intensity less than said reference level are not adjusted to an overall "bright" intensity level, (vi) determining the number of interference stripes which are not adjusted to an overall "bright" intensity level, (vii) continuously adjusting the adjustable reference level so that only the least intense interference stripe is not adjusted, (viii) continuously monitoring the translational movement, if any, of the least intense interference stripe.

9. The process of claim 8 wherein said pattern of electrical intensity is compared against said adjustable reference level on a horizontal line-by-line basis.

10. The process of claim 8 wherein at least two compensating wedges, each having a different optical path difference range, are employed.

* * * * *